(12) United States Patent
Herrmann et al.

(10) Patent No.: US 7,911,212 B2
(45) Date of Patent: Mar. 22, 2011

(54) FILTER ROD MEASURING STATION AS WELL AS METHOD FOR MEASURING THE MASS OF A SOFTENER, THE MOISTURE AND/OR THE DRY FILTER MATERIAL IN A FILTER ROD

(75) Inventors: Rainer Herrmann, Hamburg (DE); Udo Schlemm, Hamburg (DE); Wolfgang Sexauer, Freiburg (DE)

(73) Assignee: Tews Elektronik Dipl. -Ing. Manfred Tews, Hamburg (DE)

( * ) Notice: Subject to any disclaimer, the term of this patent is extended or adjusted under 35 U.S.C. 154(b) by 516 days.

(21) Appl. No.: 11/789,877

(22) Filed: Apr. 26, 2007

(65) Prior Publication Data
US 2008/0054912 A1  Mar. 6, 2008

(30) Foreign Application Priority Data

Aug. 30, 2006 (DE) .......................... 10 2006 041 191
Jan. 25, 2007 (DE) ..................... 20 2007 001 196 U

(51) Int. Cl.
*G01R 27/32* (2006.01)
(52) U.S. Cl. .......... 324/637; 324/634; 324/640; 493/39; 493/40
(58) Field of Classification Search .................. 324/633, 324/634, 637, 639, 640; 493/39, 40
See application file for complete search history.

(56) References Cited

U.S. PATENT DOCUMENTS

| | | | | |
|---|---|---|---|---|
| 5,214,969 | A |  | 6/1993 | Adkins et al. |
| 5,397,993 | A | * | 3/1995 | Tews et al. ..................... 324/634 |
| 5,977,780 | A | * | 11/1999 | Herrmann ..................... 324/640 |
| 6,922,061 | B2 | * | 7/2005 | Herrmann et al. ............. 324/633 |
| 7,027,148 | B2 | * | 4/2006 | Herrmann ..................... 324/633 |
| 2003/0206023 | A1 | * | 11/2003 | Herrmann ..................... 324/639 |
| 2005/0096202 | A1 | * | 5/2005 | Teufel et al. .................... 493/39 |

FOREIGN PATENT DOCUMENTS

| | | |
|---|---|---|
| DE | 4316723 A1 | 12/1994 |
| DE | 102004010618 A1 | 9/2005 |
| EP | 0642746 A2 | 3/1995 |
| EP | 0889321 A1 | 1/1999 |
| EP | 1197746 | 1/2001 |
| EP | 1197746 A1 | 4/2002 |
| WO | WO 03/070030 | 8/2003 |
| WO | WO03070030 A1 | 8/2003 |
| WO | WO2004065948 A2 | 8/2004 |

OTHER PUBLICATIONS

EP Search Report and Opinion in the counterpart European application EP07007952 of Jan. 22, 2008.
Sexauer et al., "Rapid determination of plasticiser content in filter rods at the making machines," CORESTA Meet. Smoke Sci.-Prod. Techno Groups, Freiburg, 2003, abstr. ST 31; XP-002465510.
Drop Through Station DT; XP-002465511, 2008.

\* cited by examiner

*Primary Examiner* — Timothy J Dole
(74) *Attorney, Agent, or Firm* — Kinney & Lange, P.A.

(57) ABSTRACT

A filter rod measuring station is equipped with measuring devices which measure at least the mass (M) of a filter rod and the draw resistance (PD) of the filter rod, and a microwave measuring device is provided for measuring the mass of the softener and/or the moisture content and/or the dry mass of the filter rod.

22 Claims, 3 Drawing Sheets

| 10 | Remove Rod from Production Process |
|---|---|
| 12 | Measure Mass |
| 14 | Microwave Measurement |
| 16 | Measure Draw Resistance |
| 18 | Measure Diameter |

| 10 | Remove Rod from Production Process |
| 12 | Measure Mass |
| 14 | Microwave Measurement |
| 16 | Measure Draw Resistance |
| 18 | Measure Diameter |

FILTER ROD MEASURING STATION AS WELL AS METHOD FOR MEASURING THE MASS OF A SOFTENER, THE MOISTURE AND/OR THE DRY FILTER MATERIAL IN A FILTER ROD

BACKGROUND

The present invention relates to a filter rod measuring station as well as a method for measuring the mass of a softener, the moisture and/or the dry filter material in a filter rod as used as a cigarette filter.

During the manufacture of cigarette filters, in a filter rod machine a plug is formed from a cellulose acetate filter tow. The plug is sprayed with a softener, the fibres of the filter material welded to one another and thus a dimensional stability is created for the filter rod. The softener, generally triacetin, provides the desired filter effect by the cross-linking of the fibres and ensures that even during a subsequent smoking process, the filter remains in shape. This is especially important as, during the smoking process, a not inconsiderable amount of water vapour also flows through the filter.

The filter effect of a cellulose acetate filter depends on the type of fibre material of the filter tow used. The fibre material of the filter tow is identified by the provision of its titre.

In addition to being dependent on the material, the filter effect also depends on the total density of the filter tow used and the type of cross-linking of the fibres. The cross-linking of the fibres is quite substantially determined by the amount of triacetin used. During the manufacture of cigarette filters it is generally desired to achieve a filter effect which is as high as possible for the tobacco smoke condensate with as little draw resistance as possible. The draw resistance is the pressure loss via a filter with constant air flow.

A method and a device for measuring the triacetin content in filter plugs, during the production thereof, is known from EP 1 197 746 A1. A microwave measuring device is used in the method which, before and after the addition of triacetin, detects two measured variables determining the mass and the moisture. The mass of the added triacetin may be determined from the measured variables obtained. The method is used in the production process line, before and after the addition of triacetin.

The simultaneous acetate and triacetin measurement according to WO 03/070030 A1 is also carried out in a machine for manufacturing cigarette filters. A measurement of the mass flow of filter tow material through the machine is carried out, as well as a measurement of the mass of softener used. In this connection a microwave measuring device is used. A measurement is also carried out with this attachment during the manufacturing process, whereby it is necessary to install two sensors in the machine, once before the addition of the softener and once after the addition of the softener.

These online methods are, however, only usable where the required space for the installation of a microwave sensor is also available on the filter plug in the filter rod machine. Moreover, with the one sensor plug method, even here the problem of the occasional production of rejects occurs by periodically disconnecting the triacetin for determining the mass of the filter rod without triacetin.

SUMMARY

The object of the invention is to measure accurately by simple means the mass of a softener, the moisture and/or the dry filter material in a filter rod.

According to the invention, the object is achieved by a filter rod measuring station and a measuring method.

The invention relates to a filter rod measuring station. Filter rod measuring stations are measuring stations configured separately from the production machines for cigarette filters. Filter rods are supplied on a sample basis to the measuring stations and their physical properties measured. The filter rod measuring station according to the invention measures at least the mass of the filter rod and the draw resistance thereof. The filter rods are supplied to the filter rod measuring station, after the softener has been applied to the filter material. During the measurement of the mass, the total mass of the filter rod is measured which is the mass of a dry filter rod relative to the mass of the applied softener and the moisture contained in the material. Dry filter material is always understood hereinafter as the mass of the filter rod without the mass of the softener and the mass of the moisture. The draw resistance is measured as the pressure loss which occurs with a constant air flow through the filter.

According to the invention, in addition to these two measured variables, a microwave measuring device is used which detects at least two further measured variables on the filter rod. The recognition underlying the invention is that for a simple and accurate measurement of the softener content in the filter rod, the draw resistance is important in combination with the other variables.

In a preferred embodiment, the filter rod measuring station is provided with a control unit to which at least the measured values for the mass, the draw resistance and two measured values of the microwave measuring device are applied. The filter rod measuring station according to the invention is configured as a separate device which is provided with an opening via which one or more filter rods to be measured may be inserted for measurement. The filter rods may therefore be removed mechanically or manually from the flow of the filter rods in the filter rod machine. The microwave measuring device has a microwave resonator and measuring means in order to detect alterations to the resonance curve. The measuring means preferably detect two characteristics of the resonance: a resonance frequency shift (A) and a widening of the resonance curve (B). The latter value is also occasionally denoted as linear shift (B). When they are evaluated together with the mass and the draw resistance, both measured variables provide a very reliable value for the added mass of softener.

In a further embodiment, the filter rod measuring station is equipped with a microwave measuring device which carries out measurements in a portion of the filter rod. Relative to the longitudinal direction of the filter rod, a measurement is carried out for a markedly shorter length of filter rod than the entire filter rod to be measured. Such measuring devices are known from EP 0 889 321 A1 in order to obtain a density and/or moisture profile in the longitudinal direction of a sample. The filter rod to be measured is, therefore, transported through a through bore, which extends through a resonator extending in a substantially planar manner. The resonator is, in this case, filled with dielectric in order to improve the measuring accuracy. Microwave resonators with a different geometry may also be filled with dielectric.

In a preferred development of the microwave measuring device, transport means are provided which transport the filter rod in its longitudinal direction through the microwave measuring device. During transportation of the filter rod, a plurality of measuring processes are carried out so that the measured values may be evaluated by an evaluation unit of the filter rod measuring station, respectively in sections for a filter rod. The evaluation unit determines, from the measured values obtained in sections, a local concentration of softeners in the filter rod. In this manner, a concentration profile may be determined in a filter rod. For evaluating a total concentration in the filter rod, the local concentration values are averaged. In this connection, different averaging methods may be used.

The object according to the invention is also achieved by a method for measuring the mass of a softener, the moisture and/or the dry filter material in a filter rod.

The method comprises the method steps of measuring the mass and the draw resistance of the filter rod to be measured and measuring at least two values associated with interactions between a microwave measuring device and the filter rod.

The method according to the invention does not take place in the machine for producing the filter (filter maker), but in a separate filter rod measuring station.

The microwave measuring device measures a detuning of the resonance frequency in the form of its shift as well as a widening of the resonance curve for a resonance generated in a resonator. With the method according to the invention, the moisture content is determined in the filter rod from the measured variables of the microwave sensor and the measured mass (M).

The determination of the mass of the softener results from two measured values of the microwave measuring device, the measured value of the mass (M) and the draw resistance (PD).

With the method according to the invention, the dry mass of the filter rod may also be determined from the measured mass of the filter rod, the mass of the softener and the mass of the water by subtraction.

In a preferred embodiment of the method according to the invention, the filter rod to be measured is removed from the production process thereof via a removal device. Subsequently, a determination of the mass is preferably carried out as a first measurement, for example as a determination of the weight by weighing. With the determination of the mass, naturally the total mass is determined, i.e. the mass due to the filter tow, the moisture contained therein and the softener used.

After the determination of the mass, the filter rod to be measured is supplied to the microwave sensor which measures at least two variables thereon.

In a subsequent step, the draw resistance on the filter rod, which occurs with constant air flow through the filter rod, is measured. The draw resistance is thus measured as the pressure loss with constant air flow through the filter rod.

In a subsequent step even the diameter (D) of the filter rod may also preferably be measured.

BRIEF DESCRIPTION OF THE DRAWINGS

The method according to the invention is described in more detail hereinafter with reference to an embodiment, as well as with reference to two curves, in which.

DESCRIPTION

Figure 1:
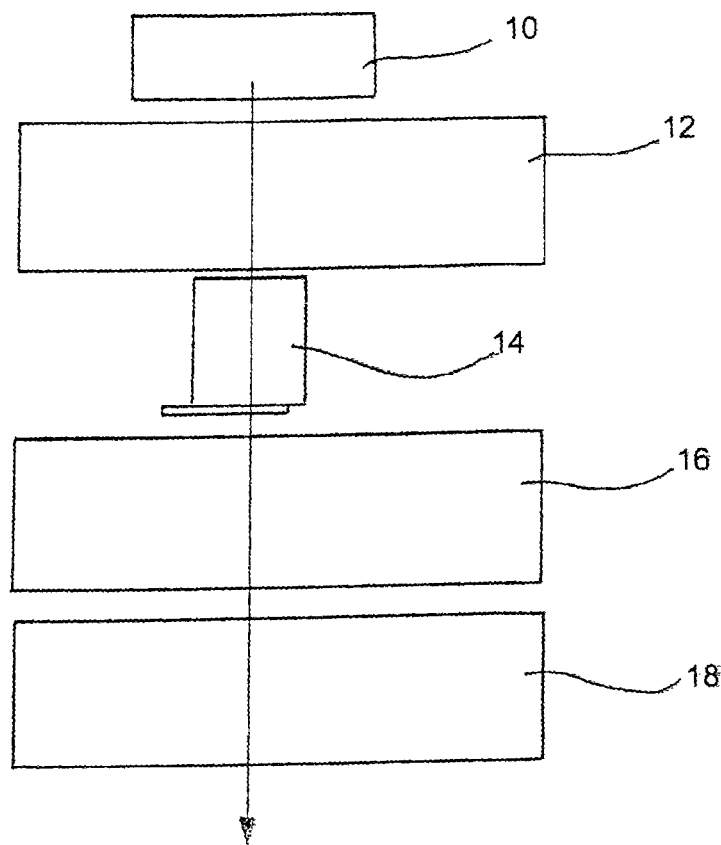
FIG. 1 shows a block diagram of the method according to the invention.

The method according to the invention is described in more detail hereinafter with reference to FIG. 1. In a first step 10 filter rods are removed from the production process manually or automatically through a filter rod hopper. The filter rod hopper supplies the removed filter rods for measuring to a filter rod measuring station. In one method step 12 in the filter rod measuring station, the mass M of the filter rod is provided. In a subsequent step 14 the filter rod is supplied to a microwave sensor. The microwave measuring device has a microwave resonator into which the filter rod to be measured is introduced. In the microwave resonator a stationary wave is formed with the resonance frequency, with which a filter rod to be measured interacts. The filter rod with its spatial expansion and its electrical properties alters the resonator so that the resonance curve occurring in the resonator is altered. Two alterations in the resonance curve are important for the measurements. On the one hand, a shift of the resonance frequency occurs. This variable is denoted by A. The second characteristic variable is the shift B of the resonance curve. The alteration A may be primarily due to the real part of the dielectric constant of the inserted filter rod, whilst the alteration B is primarily based on the imaginary part of the dielectric constant. Generally, the parameter A is used for determining the mass of the product. The ratio of the variables B/A is independent of the mass and provides an indication of the moisture content.

In step 14 the microwave sensor detects, in a manner known per se, the measured variables A and B. In a subsequent step 16, the measurement of the draw resistance (PD) is carried out which is also denoted as "pressure drop". The draw resistance specifies the pressure drop through the filter rod which is present with a defined air flow. It is important here that measurements are carried out with stationary air flow and transient effects are not considered, as occur when increasing or reducing the air flow.

In a final method step 18 the diameter of the filter rod is measured.

The data obtained in the filter measuring station are processed in an evaluation unit in the measuring station. Particularly advantageous for the measurement of the triacetin mass is the following formula:

$$M_{triacetin} = a0 + a1 \cdot A + a2 \cdot B + a3 \cdot M + a4 \cdot PD.$$

This formula is important in that the variables PD for determining the triacetin mass enter into the equation.

The moisture content is determined as:

$$M_{moisture} = b0 + b1 \cdot A + b2 \cdot B + b3 \cdot M/A,$$

even a term $b4 \cdot M/B$ being able to be considered additionally to or instead of the b3 term.

Figure 2:
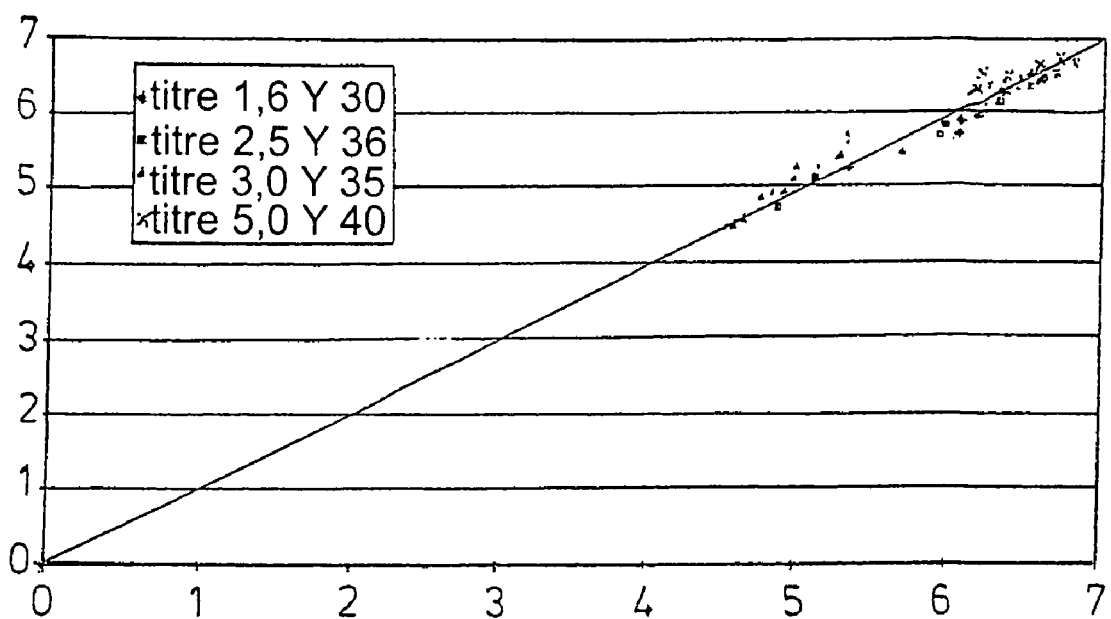
FIG. 2 shows a measurement of the triacetin value in mg in comparison with reference values.

FIG. 2 shows for different titres (1.6 Y30, 2.5 Y36, 3.0 Y35 and 5.0 Y40) the comparison between measured moisture content values on the ordinate with predetermined reference values on the abscissa. It is clearly visible that a reliable detection of the moisture is carried out with the method according to the invention. It is a distinctive feature in the determination of the moisture content in the filter rod that this is able to be carried out independently of the titre. In other words, a set of parameters (b0, b1, b2, b3) which, independently of the titre of the material, discloses the moisture content.

Figure 3:
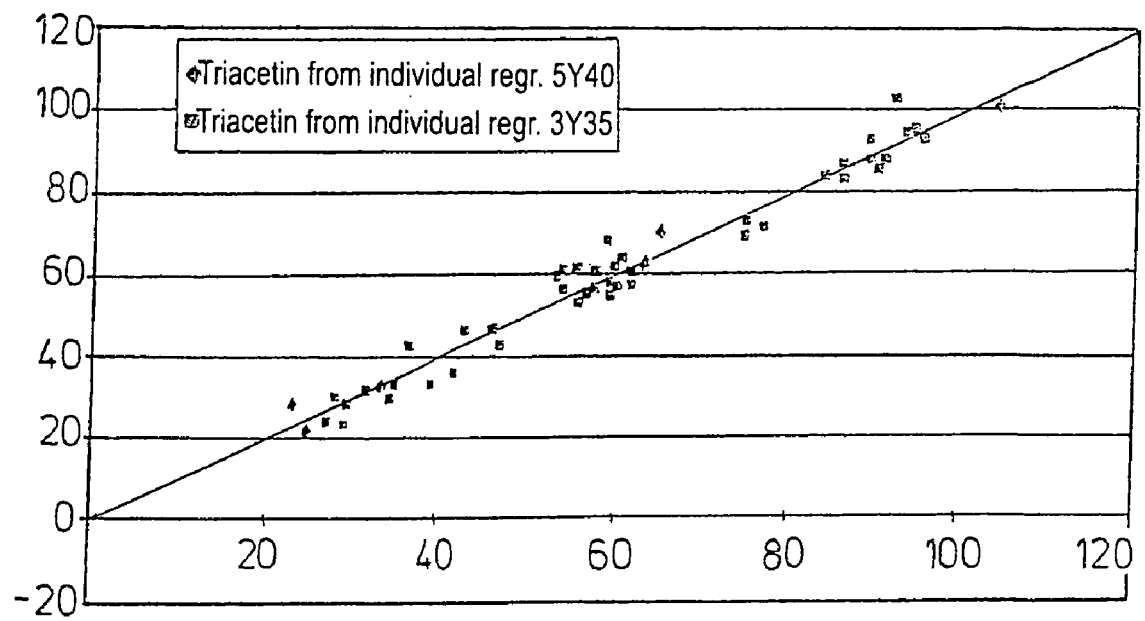
FIG. 3 shows the comparison of measured moisture values with predetermined reference values and, FIG. 4 shows a schematic view of a microwave measuring device for determining a local softener concentration.

Shown in FIG. 3 is the measurement of the triacetin content. In this connection, again the measured variables are applied to the ordinate, whilst predetermined reference values are applied to the abscissa. Also in this case the above formula is a reliable measurement for determining the triacetin mass in the filter rod. In contrast to the determination of moisture, with the determination of triacetin, the coefficient set (a0, a1, a2, a3, a4) is not independent of the titre of the material. This means that for evaluating the measured data, the titre of the material additionally has to be known in order to select the correct set of parameters.

In addition to the aforementioned formula in which the triacetin mass is detected directly dependent on the measured variables A, B, M and PD, there is also the possibility of determining the dry masses in an approximate manner via other combinations (tabular values). Thus it is known, for example, to determine the approximate dry mass from the value of the draw resistance and the diameter of the filter rod. From the dry mass, the triacetin amount may then again be determined in combination with the measured mass M and the characteristics of the microwave measuring device. Combining these tabular values for the dry mass with the microwave measured values has, therefore, the object of improving the insufficient accuracy of these tabular values and compensating for the variation in moisture effect. In contrast to the predetermined formula, consideration is additionally given in this case to the measured variables A, B, M and the draw resistance PD, as well as the diameter (D) of the filter rod. As, however, the approximate dry mass is only determined by two measured variables, this method is on the whole less accurate than that first described.

Figure 4:
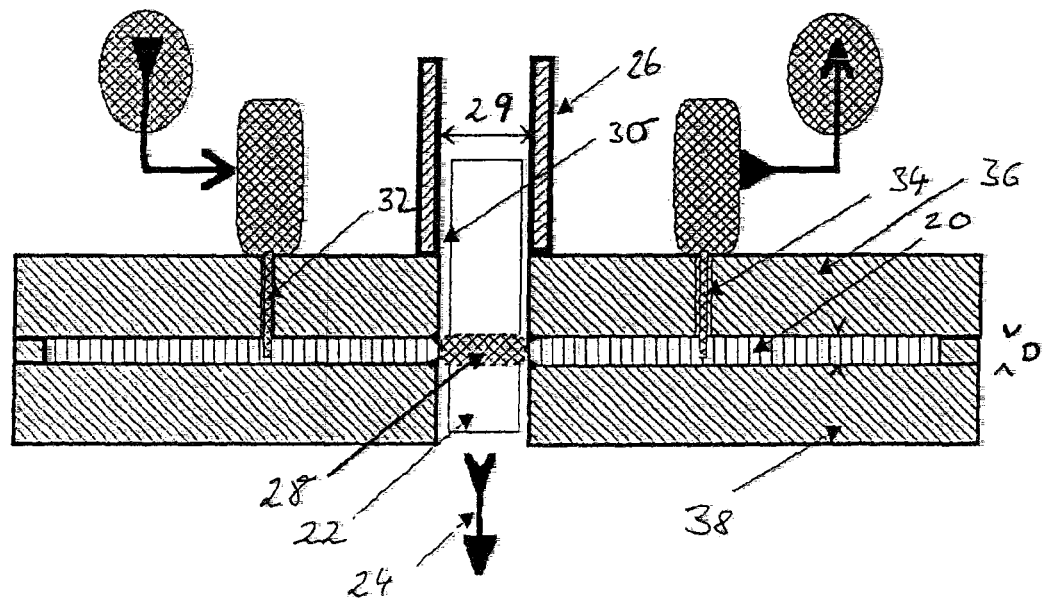

FIG. 4 shows a microwave measuring device which is suitable for measuring a triacetin profile in a filter rod. The microwave measuring device corresponds in its construction substantially to the microwave measuring device known from EP 0 889 321 A1. The microwave measuring device according to FIG. 4 has a resonator cavity 20 through which a filter rod 22 is transported in the direction 24. The filter rod 22 is supplied to the resonator cavity via a guide tube 26. Due to the selected geometry for the resonator cavity, the characteristic variables A and B are measured in a region 28. The guide tube 26 has a diameter 29 which is slightly larger than the diameter of the filter rod 22. In the region 30 the guide tube 26 is placed on the resonator body. The microwaves are fed into the resonator cavity 20 via a microwave transmitting aerial 32, where they are measured and/or again decoupled via a microwave receiving aerial 34. The resonator cavity is defined by an upper part 36 and a lower part 38. The geometry is selected in this case such that the height D is markedly smaller than the extension of the resonator cavity in its expansion transversely to the direction of transport 24. The measured values A and B provide information about the triacetin concentration in the portion 28 and thus allow by transport of the filter rod 22 a plurality of portions on a filter rod to be measured. Each individual portion may be evaluated according to the method disclosed above.

Tests have shown that when measuring, the time passed since the production of the filter rod also has an important effect. It has been shown that it is possible to operate within the first ten minutes, with a coefficient set which is time-independent. If the time duration of 10 minutes from the application of the triacetin is exceeded and thus hardening has started, it has been proved that the coefficient sets for determining the triacetin mass are altered. A determination of the triacetin mass is, however, also possible with the altered coefficient set.

In a particularly preferred embodiment, the detected measured data are processed by a control unit and compared with predetermined reference values. If the comparison shows that the triacetin value or the dry value of the processing material which is actually present deviates too sharply from the corresponding reference value, a warning signal may be triggered. The accuracy of the measurements has also shown that the measured values are, in principle, suitable for adjusting both the mass flow and the triacetin flow in the process of manufacturing the filter rod.

The invention claimed is:

1. A filter rod measuring station comprising a measuring device for measuring a mass (M) of a filter rod, a measuring device for measuring a draw resistance (PD) of the filter rod, a microwave measuring device for measuring two values (A, B) of the filter rod, and an evaluation unit programmed to determine the mass of a softener in the filter rod from the measured values (A, B) of the microwave measuring device, the measured value for the mass (M), and the measured value for the draw resistance (PD).

2. The filter rod measuring station according to claim 1, characterised by a control unit to which the measured values of the mass (M), the draw resistance (PD) and two measured values of the microwave sensor are applied.

3. The filter rod measuring station according to claim 1, characterised in that the microwave measuring device has a microwave resonator and measuring means in order to detect alterations in a resonance.

4. The filter rod measuring station according to claim 3, characterised in that the measuring means detect two measured values of the resonance.

5. The filter rod measuring station according to claim 4, characterised in that the measuring means detect a resonance frequency shift (A) and a widening of the resonance curve (B).

6. The filter rod measuring station according to claim 1, characterised in that the microwave measuring device carries out measurements in a portion of the filter rod which has a markedly shorter length than the entire filter rod to be measured, relative to the longitudinal axis of the filter rod.

7. The filter rod measuring station according to claim 6, characterised in that transport means are provided which transport the filter rod in a longitudinal direction.

8. The filter rod measuring station according to claim 6, characterised in that the evaluation unit evaluates the measured values of the microwave measuring device respectively for the portion of the filter rod that is measured by the microwave measuring device.

9. The filter rod measuring station according to claim 8, characterised in that the evaluation unit determines from the measured values a local concentration of softener in the filter rod.

10. The filter rod measuring station according to claim 9, characterised in that the evaluation unit detects the local concentration values for assessing a total concentration.

11. The filter rod measuring station according to claim 1, characterised in that the microwave measuring device is designed to detect the entire filter rod in a measuring process.

12. A method for measuring a mass of a softener, comprising the following steps:
   measuring a mass (M) and a draw resistance (PD) of the filter rod;
   measuring at least two values (A, B) of the filter rod by a microwave measuring device; and
   determining the mass of the softener in the filter rod from the measured values (A, B) of the microwave measuring device, a measured value of the mass (M), and a measured value of the draw resistance (PD).

13. The method according to claim 12, characterised in that the filter rod is inserted into a filter rod measuring station for the measurement.

14. The method according to claim 13, characterised in that the moisture content in the filter rod is determined from the measured values of the microwave measuring device and the measured mass (M).

15. The method according claim 13, characterised in that the dry mass of the filter rod is determined from the measured mass of the filter rod, less the mass of the softener and the moisture.

16. The method according to claim 13, characterised in that the filter rod to be measured is removed via a removal device from a machine for manufacturing the filter rod.

17. The method according to claim 16, characterised in that the removed filter rod is supplied to a measuring unit which measures the mass thereof.

18. The method according to claim 17, characterised in that the filter rod is supplied to the microwave measuring device.

19. The method according to claim 18, characterised in that the draw resistance of the filter rod is measured after the filter rod is supplied to the microwave measuring device.

20. The method according to claim 19, characterised in that a diameter of the filter rod is measured.

21. The method according to claim 12, characterised in that the microwave measuring device measures a resonance frequency shift (A) and a widening of the resonance curve (B) of a resonance generated in a microwave resonator in the presence of the filter rod to be measured.

22. The method of claim 12, wherein at least a moisture content of the filter rod and a dry mass of the filter rod are determined from the measured values of the microwave measuring device and the value of the mass (M) of the filter rod.

* * * * *